(12) United States Patent
Doemer et al.

(10) Patent No.: US 12,053,581 B2
(45) Date of Patent: *Aug. 6, 2024

(54) RESPIRATION DEVICE AND METHOD FOR A RESPIRATION DEVICE

(71) Applicant: Loewenstein Medical Technology S.A., Luxembourg (LU)

(72) Inventors: Benno Doemer, Ettlingen (DE); Dominic Klausmann, Freiburg (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,478

(22) Filed: Feb. 22, 2023

(65) Prior Publication Data

US 2023/0201498 A1    Jun. 29, 2023

Related U.S. Application Data

(63) Continuation of application No. 16/206,486, filed on Nov. 30, 2018, now Pat. No. 11,602,604, which is a
(Continued)

(30) Foreign Application Priority Data

Aug. 28, 2014 (DE) .......................... 102014012791.5

(51) Int. Cl.
*A61M 16/06* (2006.01)
*A61B 5/00* (2006.01)
(Continued)

(52) U.S. Cl.
CPC ....... *A61M 16/0069* (2014.02); *A61B 5/0826* (2013.01); *A61B 5/7264* (2013.01);
(Continued)

(58) Field of Classification Search
CPC ............ A61M 16/0069; A61M 16/024; A61M 16/0051; A61M 16/16; A61M 16/208;
(Continued)

(56) References Cited

U.S. PATENT DOCUMENTS 5,803,066 A * 9/1998 Rapoport ............. A61B 5/6803
128/207.18
6,138,675 A * 10/2000 Berthon-Jones ....... A61B 5/087
128/204.23
(Continued)

FOREIGN PATENT DOCUMENTS

EP    1867227 A1    12/2007
EP    2421435 A1    2/2012
(Continued)

*Primary Examiner* — Tu A Vo
(74) *Attorney, Agent, or Firm* — Abel Schillinger, LLP (57) ABSTRACT

The present invention relates to a method and a respiration device having a respiration unit for generating an airflow for the respiration and having a monitoring unit. The monitoring unit is used to detect a respiration parameter and to classify events in the respiration on the basis of monitoring of the respiration parameter. In this case, the monitoring unit is configured to carry out an event analysis to recognize an occurrence, which is characteristic for Cheyne-Stokes respiration, of chronologically successive events and for this
(Continued)

purpose to ascertain the period length thereof and to compare them to one another and to register the presence of Cheyne-Stokes respiration when the compared period lengths each deviate by less than 40% from one another.

19 Claims, 1 Drawing Sheet

Related U.S. Application Data continuation of application No. 14/834,686, filed on Aug. 25, 2015, now Pat. No. 10,159,810.

(51) Int. Cl.

| | | |
|---|---|---|
| *A61B 5/08* | (2006.01) | |
| *A61M 16/00* | (2006.01) | |
| *A61M 16/16* | (2006.01) | |
| *A61M 16/20* | (2006.01) | |
| *G16H 40/63* | (2018.01) | |
| *G16H 50/20* | (2018.01) | |

(52) U.S. Cl.
CPC ...... *A61M 16/0051* (2013.01); *A61M 16/024* (2017.08); *G16H 40/63* (2018.01); *G16H 50/20* (2018.01); *A61B 5/0816* (2013.01); *A61B 5/4818* (2013.01); *A61M 2016/0027* (2013.01); *A61M 2016/0036* (2013.01); *A61M 16/16* (2013.01); *A61M 16/208* (2013.01); *A61M 2205/50* (2013.01); *A61M 2230/04* (2013.01); *A61M 2230/10* (2013.01); *A61M 2230/14* (2013.01); *A61M 2230/205* (2013.01); *A61M 2230/42* (2013.01); *A61M 2230/60* (2013.01)

(58) Field of Classification Search
CPC .. A61M 2016/0027; A61M 2016/0036; A61M 2205/50; A61M 2230/04; A61M 2230/10; A61M 2230/14; A61M 2230/205; A61M 2230/42; A61M 2230/60; G16H 50/20; G16H 40/63; A61B 5/0826; A61B 5/7264; A61B 5/0816; A61B 5/4818
See application file for complete search history.

(56) References Cited

U.S. PATENT DOCUMENTS

| | | | | |
|---|---|---|---|---|
| 6,832,609 | B2 * | 12/2004 | Wright | A61B 5/087 128/204.23 |
| 7,070,568 | B1 | 7/2006 | Koh | |
| 11,602,604 | B2 * | 3/2023 | Doemer | G16H 40/63 |
| 2006/0070624 | A1 * | 4/2006 | Kane | A61M 16/0003 128/204.23 |
| 2006/0249149 | A1 * | 11/2006 | Meier | A61M 16/024 128/204.26 |
| 2007/0289785 | A1 | 12/2007 | Mayer | |
| 2008/0177195 | A1 | 7/2008 | Armistead | |
| 2008/0183083 | A1 | 7/2008 | Markowitz | |
| 2008/0243017 | A1 * | 10/2008 | Moussavi | A61B 5/6815 600/529 |
| 2011/0054279 | A1 | 5/2011 | Reisfeld | |
| 2011/0203588 | A1 * | 8/2011 | Armitstead | A61M 16/0003 128/204.21 |
| 2012/0016218 | A1 * | 1/2012 | Lau | A61B 5/7264 600/323 |
| 2012/0088992 | A1 * | 4/2012 | Armitstead | A61B 5/7267 600/323 |
| 2012/0190998 | A1 * | 7/2012 | Armitstead | A61M 16/0633 128/204.23 |
| 2013/0125892 | A1 * | 5/2013 | Shelly | A61M 16/0066 128/204.23 |
| 2013/0317765 | A1 * | 11/2013 | Rao | A61M 16/00 702/51 |
| 2015/0038867 | A1 * | 2/2015 | Armitstead | A61M 16/0003 128/204.23 |
| 2016/0045161 | A1 * | 2/2016 | Alshaer | A61B 5/097 600/538 |

FOREIGN PATENT DOCUMENTS

| | | | |
|---|---|---|---|
| WO | 2009118737 A2 | 10/2009 | |
| WO | 2010121290 A1 | 10/2010 | |
| WO | WO-2011023961 A1 * | 3/2011 | ............ A61B 5/01 |
| WO | 2013110136 A1 | 8/2013 | |

* cited by examiner

RESPIRATION DEVICE AND METHOD FOR A RESPIRATION DEVICE

CROSS-REFERENCE TO RELATED APPLICATIONS

The present application is a continuation of U.S. patent application Ser. No. 16/206,486, filed Nov. 30, 2018, which is a continuation of U.S. patent application Ser. No. 14/834,686, filed Aug. 25, 2015, now U.S. Pat. No. 10,159,810, which claims priority under 35 U.S.C. § 119 of German Patent Application No. 10 2014 012 791.5, filed Aug. 28, 2014. The entire disclosures of these applications are expressly incorporated by reference herein.

BACKGROUND OF THE INVENTION

Field of the Invention

The present invention relates to a method for operating a respiration device and a respiration device having at least one respiration unit for generating an airflow for respiration and having at least one monitoring unit. The monitoring unit is used to detect at least one respiration parameter and to classify events in the respiration on the basis of monitoring of the respiration parameter.

Discussion of Background Information

In the case of respiration devices, it is often advantageous if the possibility exists for recognizing respiratory disturbances during respiration. On the one hand, this enables monitoring of the efficiency of the respiration and, on the other hand, primary and secondary illnesses can be recognized better.

One form of such a respiratory disturbance is so-called Cheyne-Stokes respiration (CS respiration). CS respiration is frequently induced by defective respiratory regulation. The trigger or primary illness in this case is frequently cardiac insufficiency. CS respiration is characterized by alternating phases, which merge softly into one another, of hypoventilation (hypopnea and apnea) and hyperventilation. A relatively brief respiratory arrest can frequently also follow the shallowest breaths. The breaths then increasingly deepen thereafter.

An array of methods and devices are known in the prior art, which enable recognition of CS respiration during respiration. For example, EP 1 867 227 A2 describes CS recognition on the basis of a peak in the spectrogram, the flow, and apnea/hypopnea recognition. In addition, the measure is used for the steepness of the rebound of the respiration after hypoventilation. EP 2 421 435 A1 recognizes CS respiration on the basis of an oximeter signal via the length and the rebound of the saturation. WO 2013/110 136 recognizes CS respiration on the basis of a graph of the cycle lengths, which are used in the course of event recognition. CS recognition is performed in WO 2009/118 737 by means of determination of the start and end of apneas, calculation of time offsets between the apneas, and subsequent generation of an output on the basis of the multiple of the cycle lengths. The entire disclosures of the documents mentioned above are incorporated by reference herein.

In view of the foregoing, it would be advantageous to have available a respiration device and a method for operating a respiration device which enable reliable and uncomplicated recognition of CS respiration.

SUMMARY OF THE INVENTION

The present invention provides a respiration device and a method for a respiration device as set forth in the instant independent claims. Several advantages and features of the present invention result from the dependent claims. Further advantages and features are specified in the general description and the description of the exemplary embodiment.

The respiration device according to the invention comprises at least one respiration unit for generating an airflow for respiration and at least one monitoring unit. The monitoring unit is used to detect at least one respiration parameter and to classify events in the respiration on the basis of monitoring of the respiration parameter. In this case, the monitoring unit is able and designed to carry out at least one event analysis to recognize chronologically successive events. The event analysis is used in this case to recognize an occurrence of the events which is characteristic for CS respiration. For the event analysis, the monitoring unit is able and designed to ascertain period lengths between the events. In addition, the monitoring unit is able and designed to compare the ascertained period lengths at least partially to one another. The monitoring unit is additionally also able and designed to register the presence of CS respiration when the comparison of the period lengths has the result that the compared period lengths deviate from one another by less than 40%.

The respiration device according to the invention has many advantages. One substantial advantage is that a monitoring unit is provided, using which a characteristic occurrence of chronologically successive events is used to recognize CS respiration. The monitoring unit identifies the characteristic occurrence in this case on the basis of a comparison of the period lengths between the events and a corresponding evaluation of the deviation of specific period lengths from one another. Such a recognition of the CS respiration is very reliable, since the periodicity of specific events is an essential feature of CS respiration.

In addition, such a monitoring unit, which carries out an event analysis to recognize CS respiration, can be implemented in a comparatively uncomplicated manner. Many devices already have the capability of detecting events in respiration and recognizing them as specific types. The classified events can then be used as the foundation for the CS recognition.

In particular, a characteristic occurrence of at least two and preferably three chronologically successive events is used to recognize CS respiration. The period lengths of adjacent events are preferably compared to one another. In this case, CS respiration is registered when the period lengths between adjacent events deviate from one another by less than 40% and preferably less than 30% and particularly preferably less than 20%. In this case, events, which in particular are not considered for the ascertainment and the comparison of the period lengths, can also lie between the adjacent events.

In one advantageous refinement, the monitoring unit is able and designed to carry out at least one event analysis for recognizing an occurrence of at least three chronologically successive events which is characteristic for Cheyne-Stokes respiration and for this purpose to ascertain at least one first period length between a first event and a second event and one second period length between a second event and a third event and to at least partially compare them to one another and to register the presence of Cheyne-Stokes respiration when the first period length and the second period length deviate from one another by less than 40%.

The monitoring unit is preferably able and designed to carry out at least one event analysis of at least four chronologically successive events. The event analysis is used in this case to recognize an occurrence of the four events which is characteristic for CS respiration. For the event analysis, the monitoring unit is able and designed to ascertain at least one first period length between a first event and a second event and one second period length between a second event and a third event and one third period length between a third event and a fourth event. In addition, the monitoring unit is able and designed to compare the ascertained period lengths at least partially to one another. The monitoring unit is additionally able and designed to register the presence of CS respiration when the comparison of the period lengths has the result that the first period length and the second period length deviate from one another by less than 40% and the second period length and the third period length deviate from one another by less than 40%.

One advantage in this case is that a monitoring unit is provided, using which a characteristic occurrence of at least four chronologically successive events is used to recognize CS respiration. The error threshold is thus significantly improved.

It is also particularly advantageous for recognizing CS respiration that the monitoring unit separately checks the prescribed deviation of at most 40% in each case for two adjacent period lengths. By way of the determination of the relative deviation of the period lengths from one another, substantially more reliable recognition of CS respiration is possible than, for example, with monitoring of an absolute deviation of the period lengths. Although CS respiration is generally distinguished by a similar period length of adjacent events, the period length can nonetheless increase or decrease more strongly over multiple events. This context is taken into account by the consideration of a relative deviation of adjacent events, and the reliability of the CS recognition is increased.

It is also possible that the third period length is ascertained without the fourth event. This is performed, for example, by recognizing a combined hyper-hypoventilation event, wherein the third period length then corresponds to the event length. Other methods, e.g. statistical evaluations of event sequences, are also possible. The fourth period length is preferably also compared to the third period length, so that CS respiration can be established on the basis of the amount of the deviation from one another.

The event analysis can also comprise at least one fifth or one sixth event. The event analysis can also comprise a plurality of events. It is also possible that a large part of the events or also all events during the respiration are used for the event analysis. In this case, the comparison of the period lengths of adjacent events can be continued in the corresponding sequence. The analysis of the events can also be repeated one time or multiple times or progressively after the four events or a specific number of events, however.

In the meaning of this invention, the term period length means in particular the time between two comparable points in time within two events. For example, the period length can extend from a beginning or an end or a middle of one event to the beginning or the end or the middle of another event. It is also possible that an event may be described on the basis of a function. The period length then preferably extends from one defined value of the function of an event to another defined value of the function of an adjacent event. For example, the period length extends from a maximum of one event to a maximum of the adjacent event.

In a preferred embodiment, the monitoring unit is able and designed to register the presence of CS respiration when the first period length and the second period length and also the second period length and the third period length each deviate from one another by less than 35%. The monitoring unit particularly preferably registers CS respiration when the first period length and the second period length and also the second period length and the third period length each deviate from one another by less than 30%. A lesser deviation than the limiting value is possible, for example, 20% or less.

The period lengths preferably extend between a chronological middle of one event and a chronological middle of a following event. In particular, the monitoring unit is able and designed to calculate the period lengths starting from a chronological middle of the event. In this case, the monitoring unit is in particular able and designed to also determine the beginning and/or the end of an event. For this purpose, chronological changes of the detected respiration parameter are used in particular, which are characteristic for the beginning and/or the middle and/or the end of an event.

It is preferable for the monitoring unit to be able and designed to sort the events for the event analysis into at least two relevance classes. The two relevance classes comprise in this case in particular at least one first relevance class having events which are relevant for CS respiration. The first relevance class can also comprise events which can be used as positive features and/or negative features for the presence of CS respiration.

In particular, the two relevance classes comprise at least one second relevance class having events which are irrelevant for CS respiration. Further relevance classes having another weighting of the events can be provided.

Such a sorting of events has the advantage that the further event analysis can be performed more efficiently and substantially less complexly, since, for example, irrelevant events do not have to be analyzed further.

The sorting into the second relevance class can also be performed indirectly in the meaning of non-assignment to the first relevance class. The monitoring unit is preferably able and designed to carry out the sorting into the relevance classes before the determination of the period length. In particular, only the events of the first relevance class are subjected to the event analysis, if the sorting into the relevance classes is not included in the event analysis.

The monitoring unit is preferably able and designed to consider a previously performed classification of the events during the sorting into the relevance classes. Thus, for example, sorting can be performed depending on the event type.

In particular, the first relevance class comprises at least the events of a hyperventilation and/or a hypoventilation and/or a hypopnea and/or an apnea.

The second relevance class comprises in particular at least the events of inspiration, expiration, snoring, swallowing, speaking, nose blowing, and/or coughing, and/or a respiration interruption and/or a leak in the respiration system.

In one advantageous refinement, the monitoring unit is able and designed to sort the events of the first relevance class into at least two validity classes for the event analysis. The two validity classes preferably comprise a first validity class and a second validity class. The first validity class comprises in particular events which typically occur during CS respiration. The second validity class comprises in particular events which typically do not occur during CS respiration.

The first validity class comprises in particular events which can be used as positive features for the presence of CS respiration. The events of the second validity class can be events which indicate that CS respiration is currently not present. Such a sorting of the events into at least two validity classes simplifies the assessment of whether or not CS respiration is present.

The first validity class preferably comprises at least the events of a central apnea and/or a central hypopnea.

The second validity class preferably at least comprises the events of an obstructive apnea and/or an obstructive hypopnea.

The monitoring unit is particularly preferably able and designed to register the presence of CS respiration when at least three analyzed events and in particular three of the at least four analyzed events are chronologically successive and fulfill at least two conditions. The first condition is that at least two of the at least three events correspond to the first validity class. The second condition is that at most one event of the at least three events corresponds to the second validity class. Further conditions are possible, which regulate in particular the occurrence of specific types of events. Such an embodiment has the advantage that the monitoring unit can reliably register the presence of CS respiration by means of an assessment of positive and negative features. In particular, the three events are directly chronologically successive. In this case, at least one event, which is not considered for the event analysis, can lie between the directly following events.

In a further preferred embodiment, the monitoring unit is able and designed to register the presence of CS respiration if a first and a second and a third period length each last at least 35 seconds and preferably at least 40 seconds. The first and the second and the third period length preferably each last at least 35 seconds and preferably at least 40 seconds. The monitoring unit is also particularly preferably able and designed to register the presence of CS respiration if the first and the second and the third period length each last at most 95 seconds and preferably at most 90 seconds. Since CS respiration is generally characterized by events occurring in specific time intervals, limiting of the period length is particularly advantageous for recognizing CS respiration. At least one of the period lengths can also be determined by a statistical method or by using at least one event length.

It is possible and preferable for the monitoring unit to be able and designed to register the presence of CS respiration when a chronological duration of each one of the events taken into consideration for the event analysis is at most 80% of the period length, in particular when a chronological duration of each one of the at least four events is at most 80% of the period length. In particular, the CS respiration is registered when the chronological duration of the individual events is in each case at most 70% of the period length. The limiting value can also be less, for example, 60% or 50% or less. By way of such an embodiment, the durations of the individual events are set in a relation to the event-free time between the events, which is well suitable for recognizing CS respiration.

It is possible that the monitoring unit is able and designed to monitor a flow signal and/or a pressure signal and to analyze them on the basis of at least one algorithm, in order to classify an event. The flow signal and/or the pressure signal are provided in this case by at least one sensor unit, which is associated with the monitoring unit. The sensor unit is provided in this case for detecting at least one flow property and/or at least one pressure property of the airflow for the respiration. The analysis of flow signals or pressure signals enables reliable recognition and classification of events of the respiration.

The monitoring unit is also particularly preferably able and designed to register at least one respiration parameter, for example, the respiration frequency, the breath volume, the respiratory minute volume, the inspiration flow and/or the inspiration pressure and/or the airway resistance, on the basis of the flow signal and/or the pressure signal.

The monitoring unit can be able and designed to output a corresponding notification to a user in the event of registered CS respiration. For example, the notification can be visually and/or acoustically displayed by means of a display unit. The notification can also be output, for example, by means of an interface to at least one external data processing unit. Such a notification is particularly advantageous, since the respiration treatment can be adapted accordingly in awareness of the CS respiration. On the other hand, if the notification does not appear, corresponding success of the respiration treatment can be established.

The monitoring unit is alternatively also able and designed, in the event of registered Cheyne-Stokes respiration, to set the respiration unit to at least one respiration mode for respiration in the case of Cheyne-Stokes respiration.

The monitoring unit can also be able and designed to, in the event of registered CS respiration, output a corresponding notification to a user and/or document the CS respiration in a progressive recording of the respiration. For example, the notification can be visually and/or acoustically displayed by means of a display unit. The notification can also be output, for example, by means of an interface to at least one external data processing unit. Such a notification and/or storage of the registered CS respiration is particularly advantageous, since the respiration treatment can be adapted appropriately in awareness of the CS respiration. For example, an increase of the IPAP and/or an increase of the EPAP is suppressed in the event of registered CS respiration. Alternatively, a recommendation is output to reduce the IPAP and/or the EPAP.

The monitoring unit is alternatively also able and designed to, in the event of registered Cheyne-Stokes respiration, set the respiration unit to at least one respiration mode for respiration in the event of Cheyne-Stokes respiration, in which at least one pressure (IPAP or EPAP) is reduced.

The monitoring unit can also be able and designed to, in the event of registered CS respiration, consider it as a corresponding respiratory disturbance in a respiration statistic. Such a statistical analysis of the occurrence of CS respiration is helpful to recognize primary illnesses, for example.

It can be provided that the monitoring unit is able and designed to, in the event of registered CS respiration, set the respiration unit to at least one respiration mode which is optimized for respiration in the event of such CS respiration. Such an embodiment has the advantage that the respiration unit is automatically adapted when CS respiration is recognized. The user thus immediately obtains respiration optimized for him. In particular, the respiration mode, in the event of CS respiration, comprises at least one adaptation of a respiration parameter and preferably an anti-cyclic adaptation of the compression stroke. The automatic setting of the respiration mode can be manually deactivatable. The setting of the respiration mode is preferably noted in the respiration statistic, so that a check can be performed as to whether the changeover is advantageous for the treatment.

The method according to the invention is used for operating a respiration device having at least one respiration unit for generating an airflow for respiration. The respiration device comprises at least one monitoring unit for detecting at least one respiration parameter and for classifying events in the respiration on the basis of monitoring of the respiration parameter. In this case, at least one occurrence of chronologically successive events, which is characteristic for Cheyne-Stokes respiration, is recognized on the basis of at least one event analysis. Period lengths between the chronologically successive events are ascertained for the event analysis. The period lengths are at least partially compared to one another. The presence of Cheyne-Stokes respiration is registered when the compared period lengths deviate by less than 40% from one another.

According to the invention, the monitoring unit is able and designed to carry out at least one event analysis to recognize an occurrence of chronologically successive events, which is characteristic for Cheyne-Stokes respiration, and to ascertain respiration amplitudes for at least three chronologically successive respiration events for this purpose (inspiration and expiration) and to compare the ascertained respiration amplitudes at least partially to one another and to register the presence of Cheyne-Stokes respiration when the compared respiration amplitudes deviate by at least 25% from one another. In this case, the amplitude is preferably determined from the flow or volume of respiratory gas and results from the change of inflowing and outflowing respiratory gas. For example, the first amplitude is compared to the third amplitude, and CS respiration is recognized when the first amplitude deviates by at least 25% from the third amplitude. For example, the first amplitude is also compared to the third amplitude, and CS respiration is recognized when the first amplitude deviates by at least 50% from the third amplitude. CS respiration is also recognized when the first amplitude deviates by at least 75% from the third amplitude. For example, phases of at least temporarily very low amplitude or absent amplitude can also be displayed between the at least three chronologically successive respiration events (inspiration and expiration) or within the three respiration events. CS respiration is also recognized when phases of at least temporarily very low amplitude or absent amplitude of at least 8 seconds occur between the at least three chronologically successive respiration events (inspiration and expiration) or within the three respiration events.

According to the invention, ascertainment, storage, and display of an amplitude strength of the CS respiration are performed, i.e., consisting of hypopneas versus apneas.

According to the invention, an ascertainment is performed of a trend of the amplitude strength over hours or days or weeks as an indicator for change of an illness, for example, cardiac insufficiency or neurological illness.

According to the invention, the recognized CS respiration is confirmed or discarded by analysis of pulse oximeter signals. Cyclic variation of SpO2 or the pulse frequency or the pulse wave amplitude or the pulse transit time (PTT) are used as pulse oximeter signals. The pulse oximeter is connected in this case via an interface to the respiration device, to be able to record the data in a time-correlated manner.

According to the invention, storage and display of the ascertained period duration are performed.

According to the invention, the ascertainment of a trend of the period duration is performed over hours or days or weeks, since the period duration is an indicator of change of an illness, for example, cardiac insufficiency or neurological illness.

The method according to the invention offers an uncomplicated possibility for reliably recognizing CS respiration during respiration by a respiration device. The method is particularly preferably designed so that it is usable for operating the respiration device according to the invention and the refinements thereof. The method can thus be implemented particularly well and the advantages thereof can be used.

BRIEF DESCRIPTION OF THE DRAWINGS

Further advantages and features of the present invention result from the description of the exemplary embodiment, which is explained hereafter with reference to the appended Figures.

In the Figures.

DETAILED DESCRIPTION OF EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
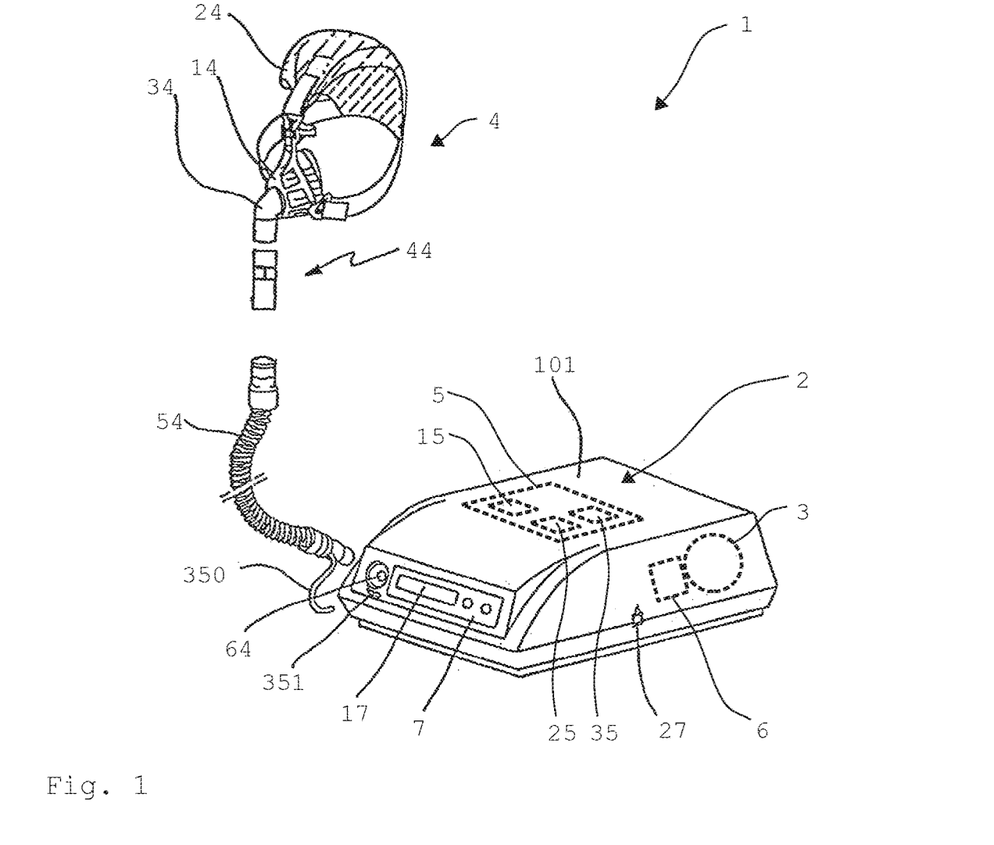
FIG. 1 shows a respiration device according to the invention.

FIG. 1 shows a respiration device 1 according to the invention in a perspective illustration. The respiration device 1 is a home respiration device in particular. The respiration device 1 is provided and designed for operation according to the method according to the invention.

The respiration device 1 comprises a respiration unit 2, which is enclosed by a housing 101, having a fan unit 3 for generating an airflow for respiration. A monitoring unit 5 having a storage unit 15, a controller 25, and a sensor unit 35 is provided for controlling the respiration unit 2.

The operation and setting of the respiration device 1 are performed via an operating unit 7 having a display unit 17 and an interface for the data exchange 27. A humidifier unit 6 is provided for increasing the moisture content of the breathing air.

The respiration device 1 has a breathing interface 4 to supply the airflow to a user for respiration. The breathing interface is preferably designed as a patient interface, which is typical in the case of respiration devices, and can be embodied, for example, as a full face mask or as a nasal pillow or as a tube or as a larynx mask. The breathing interface 4 shown here is a breathing mask 14 designed as a nasal mask. Headgear 24 is provided for fixing the breathing mask 14.

A connection hose 54, which is connected by means of a coupling unit 64 to the respiration unit 2, is provided for connecting the breathing interface 4 to the respiration unit 2. The connection hose 54 is connected to the breathing interface 4 via a coupling element 34. An expiration element 44, which comprises a valve or is designed as a valve, is arranged between the connection hose 54 and the coupling element 12. The expiration element 44 is provided in particular to prevent breathing out into the respiration device 1 during the expiration of the user.

The monitoring unit 5 is operationally connected to the sensor unit 35, which has one or more sensors for detecting variables which are characteristic for the respiration parameter. For example, the sensor unit 35 has a pressure sensor (not shown here), which detects the pressure conditions in the region of the breathing interface. For this purpose, the pressure sensor has a flow connection via a pressure measurement hose 350 to the breathing interface 4.

The pressure measurement hose 350 extends in this case from the breathing interface 4 along the connection hose 54 to an intake nozzle 351 on the housing 101. The pressure measurement hose 350 has a flow connection to the pressure sensor of the sensor unit 35 via the intake nozzle 351.

The flow measurement is performed in this case via a throttle, which is arranged in the main channel of the flow connection between fan unit 3 and breathing interface 4. An arrangement in a secondary channel is also possible. To be able to monitor further respiration parameters, the sensor unit 35 can also be equipped with sensors for measuring the respiratory excursion, for measuring an oxygen saturation of the blood, and/or for measuring EEG, EMG, EOG, or EKG activity.

Furthermore, the monitoring unit 5 has a controller 25 for activating the fan unit 3. The controller 25 provides a required minimum pressure and compensates for pressure variations which are caused by the respiration activity of the user. For example, the controller 25 also detects the current pressure in the breathing mask 14 and adjusts the output of the fan unit 3 accordingly, until a desired respiration pressure is applied.

The respiration device 1 shown here can be designed as a fixed level device or also as an automatic level device. In particular, regulation to setpoint values, which were previously calculated individually and fixed on the basis of the characteristic respiration of a user, is performed in this case by the monitoring unit 5.

It is also possible that the respiration unit 2 is adapted dynamically and in particular according to the respiration phase of the user. For example, a respiration phase change can be recognized on the basis of the monitoring unit 5, so that a higher or lower pressure can be provided depending on the respiration phase. For example, the respiration device 1 can be designed as a CPAP or APAP device. The respiration device 1 can also be designed as a bilevel device. For example, the respiration device 1 reacts to specific respiration events, for example, snoring, shallow breathing, and/or obstructive pressure spikes, with corresponding settings of the respiration parameters.

Using the respiration device 1 shown here, events which occur in the respiration or during the respiration are recognized and classified. For this purpose, the sensor unit 35 detects one or more respiration parameters and supplies corresponding signals to the monitoring unit 5, for example, a flow signal and/or a pressure signal. The monitoring unit 5 analyzes the signals by means of suitable algorithms, so that characteristic signal curves can be recognized and classified as an event. In this case, for example, a parameter extraction can be used with respect to level and amplitude values, time intervals, envelopes, zero crossings, and slopes. During an analysis with regard to time features, for example, periodicities and frequencies are used in a parameter extraction.

The recognized events can then be stored in the storage unit 15 and used for a respiration statistic. One advantage of the event recognition is that an adaptation of the respiration can be performed based on the classified events, for example, an automatic pressure increase in the event of obstructive apnea. In addition, a diagnosis of specific respiratory disturbances can be performed to a certain extent.

A particular advantage of the respiration device 1 shown here is the monitoring unit 5, which further analyzes the recognized events and registers CS respiration on the basis of a characteristic occurrence of the events. Such an event analysis 8 is outlined as an example in FIG. 2.

Figure 2:
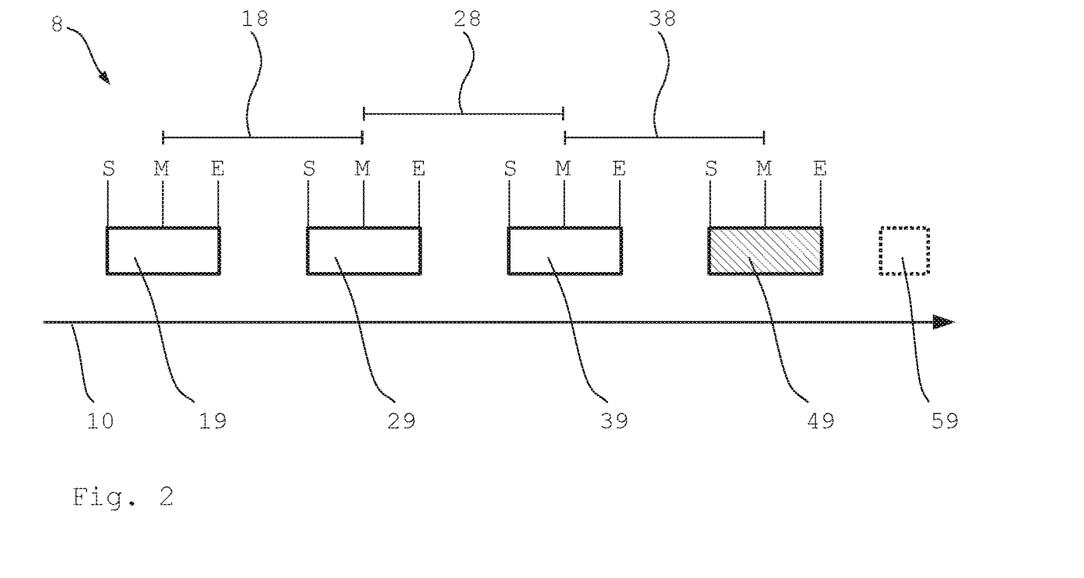
FIG. 2 shows an outlined event analysis.

FIG. 2 shows five exemplary events 19, 29, 39, 49, 59, which were detected and classified during a time 10. The first and the second and also the third event 19, 29, 39 each correspond here to a central apnea occurring in the respiration. The fourth event 49 corresponds to an obstructive apnea. The fifth event 59 stands here for a snore occurring during the respiration. Further events (not shown here) can have occurred and can have been detected between the individual events 19, 29, 39, 49, 59, for example, a hyperventilation.

For the event analysis 8, the monitoring unit 5 firstly sorts the events according to their relevance with respect to CS respiration. In this case, for example, a central hypopnea and a central apnea are relevant. The monitoring unit 5 therefore classifies the first, second, third, and fourth events as relevant for CS recognition and sorts them, for example, into a first relevance class. The fifth event 59, which is classified as a snore, is considered to be irrelevant for the CS recognition and is sorted by the monitoring unit 5, for example, into a second relevance class. For the further event analysis 8, the monitoring unit 5 then only still considers the events of the first relevance class.

Subsequently, the monitoring unit 5 analyzes the occurrence of the relevant events over the time 10. For this purpose, the monitoring unit 5 ascertains the moment of the start S, the moment of the end E, and the chronological middle of each of the relevant events. Subsequently, the period lengths are determined, which each extend from the middle M of one event to the chronological middle M of the subsequent event. A first period length 18 thus results between the first and second events 19, 29, a second period length 28 results between the second and third events 29, 39, and a third period length 38 results between the third and fourth events 39, 49.

In a next step, the monitoring unit 5 compares the first period length 18 to the second period length 28. If the comparison results in a maximum deviation of 30% of the period lengths 18, 28 from one another, it is registered as an indication of CS respiration. Subsequently, the deviation between the second period length 28 and the third period length 38 is also ascertained and, in the event of a maximum deviation of 30%, is evaluated as a further indication of the presence of CS respiration. In this case, still more than four events can also be analyzed and taken into consideration for the event analysis 8, so that the comparison also extends over further adjacent period lengths.

The monitoring unit 5 uses the respective value of the period length between the events as a further indication of the presence of CS respiration. In this case, the presence of CS respiration is presumed when the period lengths are each at least 40 seconds and at most 90 seconds.

Subsequently, the monitoring unit 5 checks the ratio between the chronological duration of one event and the associated period length. For example, the duration of the first event 19 from the start S to the end E is ascertained and compared to the first period length 18. The monitoring unit 5 registers an indication of CS respiration in this case when the chronological duration is at most 70% of the associated period length. The chronological duration of the second and third events 29, 39 is accordingly compared to the respective associated period length 28, 38 and analyzed.

Subsequently, the events sorted as relevant are validated by the monitoring unit 5. In this case, events are classified as valid when they typically occur during CS respiration. The events are classified as invalid which typically do not occur during CS respiration or the single or multiple occurrence of which negates CS respiration. For example, a central apnea or hypopnea are considered to be valid events. An obstructive apnea or hypopnea are considered to be invalid, for example.

In this case, the monitoring unit 5 sorts the events into a first validity class and a second validity class. The first validity class comprises here the first, second, and third events 19, 29, 39, which were each classified as apnea. The fourth event 49, which was classified as obstructive hypopnea, is sorted into the second validity class.

Subsequently, the monitoring unit 5 considers the number of the events sorted into the first and the second validity classes together with the total number of all events considered in the event analysis in the sense of a conclusiveness test. In the example shown here having four relevant events, the presence of CS respiration is assumed if, of three events, at least two are classified as valid events and at most one is classified as an invalid event.

The differentiation between a central apnea, which can be classified as a valid event, and an invalid obstructive apnea is preferably executed by the monitoring unit 5 on the basis of an analysis of the flow signal and the pressure signal. The signals are tapped between the breathing interface 4 and the expiration element 44. The beginning of an apnea is recognized on the basis of a flow variation and the end of the apnea is recognized on the basis of a pressure variation.

The end of the apnea can also be recognized by the occurrence of a pressure variation or flow variation, however. The delimitation of an obstructive apnea is performed in this case by the occurrence of a short, additional pressure increase at the end of the apnea. To delimit the pressure increase from possible artifacts, for example, movements or heartbeat of the user, a corresponding limiting value can be defined. In addition, the pressure increase is so short that it is substantially shorter than typical respiration periods and therefore can be delimited therefrom.

The event analysis 8 is preferably performed in consideration of agreements on the recognition of respiratory disturbances. For example, the AASM manual describes corresponding rules for event recognition and classification, which are to be taken into consideration during the analysis. The monitoring unit 5 is in particular able and designed to consider these rules during the event analysis for recognizing the CS respiration in a corresponding manner. Corresponding queries and/or algorithms are stored in the monitoring unit 5.

For example, to recognize CS respiration, at least five central apneas and/or central hypopneas per hour during the sleep of the user must occur in conjunction with the typical pattern of an increase and flattening of the respiration over at least two hours of observation time. In addition, it is possible that central apneas which occurred during already recognized CS respiration are considered as individual apneas and incorporated accordingly in the event analysis 8.

If the event analysis 8 has the result that CS respiration is present, this can be stored on the basis of a corresponding entry in a respiration statistic. The user can retrieve the respiration statistic, for example, via the interface 27 and use it to judge the respiration therapy. Depending on the frequency of the CS respiration, a manual or program-assisted changeover of the respective respiration parameters can then also be performed. The monitoring unit 5 can, in the event of an occurrence of CS respiration, also perform an automatic adaptation of the respiration unit 2 and recalculate corresponding setpoint values for respiration parameters. For example, a specific therapy mode can be set, which the CS respiration provides by anti-cyclic regulation of the compression stroke.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

To sum up, the present invention provides:

1. A respiration device, wherein the device comprises at least one respiration unit for generating an airflow for respiration and at least one monitoring unit for detecting at least one respiration parameter and for classifying events in the respiration on the basis of monitoring of the respiration parameter, the monitoring unit being able and designed to carry out at least one event analysis to recognize an occurrence of chronologically successive events which is characteristic for Cheyne-Stokes respiration and for this purpose to ascertain period lengths between the chronologically successive events and to compare the ascertained period lengths at least partially to one another and to register the presence of Cheyne-Stokes respiration when the compared period lengths deviate by less than 40% from one another.

2. The respiration device according to item 1, wherein the monitoring unit is able and designed to carry out at least one event analysis for recognizing an occurrence of at least three chronologically successive events which is characteristic for Cheyne-Stokes respiration and for this purpose to ascertain at least one first period length between a first event and a second event and one second period length between a second event and a third event and to at least partially compare them to one another and to register the presence of Cheyne-Stokes respiration when the first period length and the second period length deviate from one another by less than 40%.

3. The respiration device according to any one of items 1 and 2, wherein the monitoring unit is able and designed to carry out at least one event analysis for recognizing an occurrence of at least four chronologically successive events which is characteristic for Cheyne-Stokes respiration and for this purpose to ascertain at least one first period length between a first event and a second event and one second period length between a second event and a third event and one third period length between a third event and a fourth event and to at least partially compare them to one another and to register the presence of Cheyne-Stokes respiration when the first period length and the second period length and also the second period length and the third period length each deviate by less than 40% from one another.

4. The respiration device according to item 3, wherein the monitoring unit is able and designed to register the presence of Cheyne-Stokes respiration when the first period length and the second period length and also the second period length and the third period length each deviate by less than 35% and in particular by less than 30% from one another.
5. The respiration device according to any one of the preceding items, wherein the period lengths extend between a chronological middle of one event and a chronological middle of a following event.
6. The respiration device according to any one of the preceding items, wherein the monitoring unit is able and designed to sort the events into at least two relevance classes, comprising at least one first relevance class having events which are relevant for Cheyne-Stokes respiration and at least one second relevance class having events which are irrelevant for Cheyne-Stokes respiration.
7. The respiration device according to item 6, wherein the first relevance class comprises at least the events of a hyperventilation and/or a hypoventilation and/or a hypopnea and/or an apnea and/or the second relevance class comprises at least the events of inspiration, expiration, snoring, swallowing, speaking, nose blowing, and/or coughing, and/or a respiration interruption and/or a leak.
8. The respiration device according to any one of items 5 to 7, wherein the monitoring unit is able and designed to sort the events of the first relevance class into at least two validity classes for the event analysis, comprising a first validity class having events which typically occur in the case of Cheyne-Stokes respiration and a second validity class having events which typically do not occur in the case of Cheyne-Stokes respiration.
9. The respiration device according to any one of items 5 to 8, wherein the first validity class comprises at least the events of a central apnea and/or a central hypopnea and/or the second validity class comprises at least the events of an obstructive apnea and/or an obstructive hypopnea.
10. The respiration device according to any one of items 7 to 9, wherein the monitoring unit is able and designed to register the presence of Cheyne-Stokes respiration when at least three events occur in chronological succession and in this case at least two of the at least three events correspond to the first validity class and at most one event of the at least three events corresponds to the second validity class.
11. The respiration device according to any one of the preceding items, wherein the monitoring unit is able and designed to register the presence of Cheyne-Stokes respiration when a first and a second and a third period length are each at least 35 seconds and at most 95 seconds.
12. The respiration device according to any one of the preceding items, wherein the monitoring unit is able and designed to register the presence of Cheyne-Stokes respiration when a chronological duration of each one of the events taken into consideration for the event analysis is at most 80% and in particular at most 70% of the period length.
13. The respiration device according to any one of the preceding items, wherein the monitoring unit is able and designed to monitor at least one flow signal and/or at least one pressure signal from at least one associated sensor unit to detect at least one flow property and/or at least one pressure property of the airflow for the respiration and to analyze it on the basis of at least one algorithm, in order to classify an event.
14. The respiration device according to any one of the preceding items, wherein the monitoring unit is able and designed to output a corresponding notification to a user in the event of registered Cheyne-Stokes respiration and/or to consider it as a corresponding respiratory disturbance in a respiration statistic.
15. A method for operating a respiration device comprising at least one respiration unit for generating an airflow for respiration and at least one monitoring unit for detecting at least one respiration parameter and for classifying events in the respiration on the basis of monitoring of the respiration parameter, wherein, on the basis of at least one event analysis, at least one occurrence of chronologically successive events is recognized, which is characteristic for Cheyne-Stokes respiration, and for the event analysis, period lengths are ascertained between the chronologically successive events and at least partially compared to one another, and the presence of Cheyne-Stokes respiration is registered when the compared period lengths deviate from one another by less than 40%.

LIST OF REFERENCE NUMBERS 1 respiration device
2 respiration unit
3 fan unit
4 breathing interface
5 monitoring unit
6 humidifier unit
7 operating unit
8 event analysis
10 time
14 breathing mask
15 storage unit
17 display unit
18 period length
19 event
24 headgear
25 controller
27 interface
28 period length
29 event
34 coupling element
35 sensor unit
38 period length
39 event
44 expiration element
49 event
54 connection hose
59 event
64 coupling unit
101 housing
350 pressure measurement hose
351 intake nozzle

What is claimed is:
1. A respiration device, wherein the device comprises at least one respiration unit for generating an airflow for respiration and at least one monitoring unit for detecting at least one respiration parameter and for classifying events in the respiration on a basis of monitoring the at least one respiration parameter, the monitoring unit being configured to monitor at least one flow signal and/or at least one pressure signal from at least one associated sensor unit to detect at least one flow property and/or at least one pressure property of an airflow for the respiration and to analyze the at least one flow signal and/or at least one pressure signal in order to classify a plurality of respiration events, and further being configured to sort the classified events into at least two classes comprising at least one first class comprising the classified events
which are relevant for CS (Cheyne-Stokes) respiration and at least one second class comprising the classified events which are irrelevant for CS respiration, wherein the monitoring unit is configured to recognize an occurrence of chronologically successive events which is characteristic of CS respiration, to ascertain respiration amplitudes for at least three chronologically successive inspiration and expiration events, and to compare the ascertained respiration amplitudes to one another and to register a presence of CS respiration when the compared respiration amplitudes deviate by at least 25% from one another.

2. The respiration device of claim 1, wherein the events of the first class comprise at least events of a hyperventilation and/or a hypoventilation and/or a hypopnea and/or an apnea and/or the events of the second class comprise at least events of inspiration, expiration, snoring, swallowing, speaking, nose blowing, and/or coughing, and/or a respiration interruption and/or a leak.

3. The respiration device of claim 1, wherein the monitoring unit is configured to sort the events of the first class into at least two validity classes for the event analysis, comprising a first validity class comprising events which typically occur in a case of CS respiration and a second validity class comprising events which typically do not occur in the case of CS respiration.

4. The respiration device of claim 3, wherein the events of the first validity class comprise at least events of a central apnea and/or a central hypopnea.

5. The respiration device of claim 3, wherein the events of the second validity class comprise at least events of an obstructive apnea and/or an obstructive hypopnea.

6. The respiration device of claim 3, wherein the monitoring unit is configured to register a presence of CS respiration when at least three events of the first class occur in chronological succession and in this case at least two of the at least three events correspond to the first validity class and at most one event of the at least three events corresponds to the second validity class.

7. The respiration device of claim 6, wherein at least four events of the first class are analyzed.

8. The respiration device of claim 3, wherein the monitoring unit considers a number of respiration events sorted into the first and the second validity classes together with a total number of all respiration events considered in an event analysis by using a conclusiveness test.

9. The respiration device of claim 3, wherein a differentiation between a central apnea, classified as a valid event, and an invalid obstructive apnea is carried out by the monitoring unit on a basis of an analysis of the at least one flow signal and the at least one pressure signal.

10. The respiration device of claim 9, wherein a beginning of an apnea is recognized on a basis of a flow variation and an end of the apnea is recognized on a basis of a pressure variation and/or a flow variation.

11. The respiration device of claim 10, wherein obstructive apnea is detected by an occurrence of a short, additional pressure increase at the end of the apnea.

12. The respiration device of claim 1, wherein the device is configured to output a corresponding notification to a user in the event of registered CS respiration.

13. The respiration device of claim 1, wherein the device is configured, in the event of registered CS respiration, to set the respiration unit to at least one respiration mode for respiration in a case of CS respiration.

14. The respiration device of claim 1, wherein ascertainment, storage, and display of an amplitude strength of the CS respiration, consisting of hypopneas versus apneas, are performed.

15. The respiration device of claim 1, wherein recognized CS respiration is confirmed or discarded by analysis of pulse oximeter signals.

16. The respiration device of claim 15, wherein pulse frequency or pulse wave amplitude or pulse transit time (PTT) are used as pulse oximeter signals.

17. The respiration device of claim 15, wherein the pulse oximeter is connected to the respiration device via an interface, to be able to record data in a time-correlated manner.

18. The respiration device of claim 1, wherein the monitoring unit uses a value of a period length between respiration events as a further indication of a presence of CS respiration.

19. The respiration device of claim 18, wherein the presence of CS respiration is presumed when period lengths are each at least 40 seconds and at most 90 seconds.

* * * * *